United States Patent
Batchelor et al.

(10) Patent No.: US 9,011,433 B2
(45) Date of Patent: Apr. 21, 2015

(54) BIPOLAR COLPOTOMY DEVICE

(71) Applicant: Gyrus ACMI, Inc., Southborough, MA (US)

(72) Inventors: Kester J. Batchelor, Mound, MN (US);
Nikhil M. Murdeshwar, Maple Grove, MN (US); Tracey L. Dobbs, Delano, MN (US); Jyue Boon Lim, New Brighton, MN (US); Tsuyoshi Hayashida, Maple Grove, MN (US); Riyad Moe, Waunakee, WI (US)

(73) Assignee: Gyrus ACMI, Inc., Southborough, MA (US)

( * ) Notice: Subject to any disclaimer, the term of this patent is extended or adjusted under 35 U.S.C. 154(b) by 179 days.

(21) Appl. No.: 13/835,168

(22) Filed: Mar. 15, 2013

(65) Prior Publication Data

US 2014/0276812 A1    Sep. 18, 2014

(51) Int. Cl.
*A61B 18/18*      (2006.01)
*A61B 18/14*      (2006.01)
*A61B 17/42*      (2006.01)
*A61B 18/00*      (2006.01)

(52) U.S. Cl.
CPC ..... *A61B 18/1485* (2013.01); *A61B 2017/4216* (2013.01); *A61B 2018/00285* (2013.01); *A61B 2018/00559* (2013.01); *A61B 2018/00601* (2013.01); *A61B 2018/00625* (2013.01); *A61B 2018/1407* (2013.01)

(58) Field of Classification Search
CPC .................. A61B 18/1485; A61B 2017/4216; A61B 2018/00559; A61B 18/14
USPC .......................................................... 606/41
See application file for complete search history.

(56) References Cited

U.S. PATENT DOCUMENTS

| 4,775,362 A | 10/1988 | Kronner |
| 5,209,754 A | 5/1993 | Ahluwalia |
| 5,520,698 A | 5/1996 | Koh |
| 5,569,284 A | 10/1996 | Young et al. |
| 5,643,285 A | 7/1997 | Rowden et al. |
| 5,840,077 A | 11/1998 | Rowden et al. |
| 5,997,547 A | 12/1999 | Nakao et al. |

(Continued)

FOREIGN PATENT DOCUMENTS

| DE | 10 2009 018 521 A1 | 10/2010 |
| EP | 2 243 437 A1 | 10/2010 |
| GB | 2479582 A | 10/2011 |

OTHER PUBLICATIONS

May 12, 2014 Search Report issued in International Patent Application No. PCT/US2013/075935.

(Continued)

*Primary Examiner* — Robert N Wieland
(74) *Attorney, Agent, or Firm* — Oliff PLC (57) ABSTRACT

A bipolar electrosurgical assembly is for use in female pelvic surgical procedures. A first shaft includes a uterine manipulator, a second shaft that fits over the first shaft includes a colpotomy cup and first and second electrodes, and a third shaft can be provided over the second shaft and carries a seal for maintaining pneumoperitoneum. The colpotomy cup uses the first and second electrodes for resecting uterine tissue. Incision and resection may be performed by positioning the colpotomy cup near the cervico-vaginal junction, activating the first electrode, and moving one or both of the electrodes.

18 Claims, 8 Drawing Sheets

(56) References Cited

U.S. PATENT DOCUMENTS

| | | |
|---|---|---|
| 6,537,273 B1 | 3/2003 | Sosiak et al. |
| 7,806,894 B1 | 10/2010 | Rosenblatt et al. |
| 8,192,444 B2 | 6/2012 | Dycus |
| 2001/0021854 A1* | 9/2001 | Donnez et al. ............ 606/119 |
| 2009/0192510 A1 | 7/2009 | Bahney |
| 2012/0109124 A1 | 5/2012 | Morozov |
| 2012/0323079 A1 | 12/2012 | Bakare et al. |
| 2012/0330324 A1 | 12/2012 | Sauer |

OTHER PUBLICATIONS

Con Med: VCare Device, Marketing Brochure, Jun. 2010, Utica, NY.

Cooper Surgical: Koh Cup, Marketing Brochure, Oct. 2006, Trumbull, CT.

Cooper Surgical: Uterine Manipulator, Marketing Brochure, Feb. 2008, Trumbull, CT.

Aug. 29, 2014 Search Report and Written Opinion issued in International Patent Application No. PCT/US2013/075935.

* cited by examiner

BIPOLAR COLPOTOMY DEVICE

BACKGROUND

This disclosure relates to surgical instruments, and in particular to electrosurgical instruments utilized in total laparoscopic hysterectomy (TLH) procedures.

Electrosurgical instruments used to resect a patient's cervix from the vagina are known. Such instruments generally carry out a number of functions: positioning of the uterus for resection, maintaining pneumoperitoneum during tissue resection, aiding in physician visibility during resection, and incision and resection of a patient's cervix from the vagina. It is known to provide a colpotomy device having an electrosurgical element and a uterine manipulator to aid in incising and positioning the uterus for resection.

It is also known for the incision and resection to be performed by two electrosurgical instruments. Although one electrosurgical instrument may be introduced vaginally, at least one other electrosurgical instrument is typically introduced laparoscopically into the abdomen through a trocar or other similar device.

In general, the incision and resection are performed by a single electrosurgical instrument. This is typically introduced laparoscopically into the abdomen through a trocar or other similar device.

Instead of an electrosurgical instrument, mechanical cutting instruments such as scissors are sometimes used to form the incision.

Some known electrosurgical instruments make use of a colpotomy cup in order to position and manipulate the uterus for resection. These can take many forms, but generally have a leading edge which fits at or near the cervico-vaginal junction. Colpotomy cups sometimes also carry a monopolar electrosurgical cutting instrument, either attached to the cup, or attached to another apparatus located near the patient's uterus.

Monopolar devices exist for performing the incision to sever the cervix from the vagina. The active electrode performs the cutting in these configurations, with the return electrode placed elsewhere on the body.

SUMMARY

Some electrosurgical devices used in TLH procedures make use of monopolar electrosurgical elements. Monopolar electrosurgical elements are used with a separate return electrode (for example, a return pad, grounding patch or neutral electrode) that is placed some distance away from the incision site. As a result of the distance between the return electrode and the incision site, monopolar electrosurgical elements typically exhibit poorer control over application of energy to the incision site. In particular, monopolar electrodes deliver less controllable pulses of energy and/or higher voltages, which can result in increased heat at the surgical site, and potentially damage other tissues, such as nerves, ureters or colon tissue near that site. A risk particular to TLH procedures is over-shortening of the vagina during resection of the cervix from the vagina. This can be caused, for example, by creating too much heat at the cutting device while performing the cervico-vaginal incision. Another potential complication related to creating too much heat during cutting is known as dehiscence. This occurs when the incised tissues that are brought together to close the vaginal canal with sutures during the procedure fail to fuse before the suture absorption period is reached. This is due to the heat damage to the tissue preventing the desired healing.

A bipolar electrosurgical configuration reduces the risks associated with monopolar elements because a bipolar instrument has a shorter distance of electrical energy travel between the tissue to be excised and a return electrode. This enables the cutting energy to be more precisely focused. It also allows for lower cutting voltages to be used.

In order to overcome difficulties inherent to the TLH procedure, namely, poor visibility, poor maneuverability, high degree of clinical skill needed, difficulty of incision, thermal damage at the vaginal cuff and the risks of damaging other organs, over-shortening the patient's vagina or risking future dehiscence, an aspect of the invention relates to a bipolar electrosurgical assembly that includes a colpotomy cup and first and second electrodes, one of which is an active electrode and one of which is a return electrode. In addition, the assembly preferably includes a uterine manipulator, to be used in tandem with the colpotomy cup for positioning of the uterus, and a seal for maintaining pneumoperitoneum.

According to some embodiments, three shafts are utilized in the bipolar colpotomy assembly. The first shaft includes a uterine manipulator with a proximal end and a distal end. The second shaft is rotatably and slidably mounted over the first shaft, and preferably includes a control near its proximal end for controlling the colpotomy cup located near its distal end, and the first and second electrodes. A third shaft is rotatably and slidably mounted over the second shaft, and includes a seal for maintaining pneumoperitoneum. The seal can be, for example, a vaginal balloon, a foam plug, or malleable discs. During use, the colpotomy cup is placed at the cervico-vaginal junction, and a voltage differential can be applied between the electrodes in order to perform the incision, while the manipulator positions the cervix/uterus for resection and the seal maintains pneumoperitoneum.

According to some embodiments, the first electrode and the second electrode are on a rim at the distal open end of the colpotomy cup. The first, active, electrode can be annular, and located in a radially outer position on the rim. The first electrode can be a solid ring, or made up of multiple arcs around the rim. The second, return electrode, can be located in a radially inner position along the rim. The incision at the cervico-vaginal junction can be performed by this embodiment in one of two ways: by emitting energy from the first electrode while longitudinally advancing the colpotomy cup, or by rotating the colpotomy cup while emitting energy from the first electrode. If cutting is to be performed in the first way, the colpotomy cup rim may have different heights (i.e., the rim of the cup may have undulations such that it is wavy) so that as it is advanced, the cutting voltage will be applied to different parts of the electrodes as those different parts come into contact with tissue.

According to some embodiments, the first (active) electrode protrudes from the rim of the colpotomy cup, while the second electrode forms a ring around the rim of the colpotomy cup. In these embodiments, the second electrode may be annular along the inner portion of the rim of the colpotomy cup, and cover substantially the whole circumference of the rim, or any portion thereof. In embodiments where the first electrode is integral with and protrudes from the colpotomy cup, incision is performed by emitting energy from the first electrode while rotating the colpotomy cup, which rotates the first electrode.

According to another embodiment, the first electrode is mounted on a spindle that rotates about the second shaft, and the second electrode is located along the distal edge of the colpotomy cup. The colpotomy cup is fixedly mounted to the second shaft, and stays fixed while the spindle performs the incision by emitting energy and rotating about the axis of the second shaft.

According to another embodiment, the colpotomy cup is made up of two cups, one inner cup and one outer cup. The inner cup is fixedly mounted to the second shaft and carries the second electrode along its rim, and the outer cup is rotatably mounted to the second shaft and carries the first electrode along all or a part of its rim. Incision is performed while rotating the outer cup about the axis of the second shaft.

BRIEF DESCRIPTION OF THE DRAWINGS

Various exemplary embodiments of the disclosed electrosurgical instrument will be described in detail with reference to the following drawings in which.

DETAILED DESCRIPTION OF EMBODIMENTS

The following exemplary embodiments are described below with reference to the figures in the context of female pelvic surgery, and in particular total laparoscopic hysterectomy.

Figure 1:
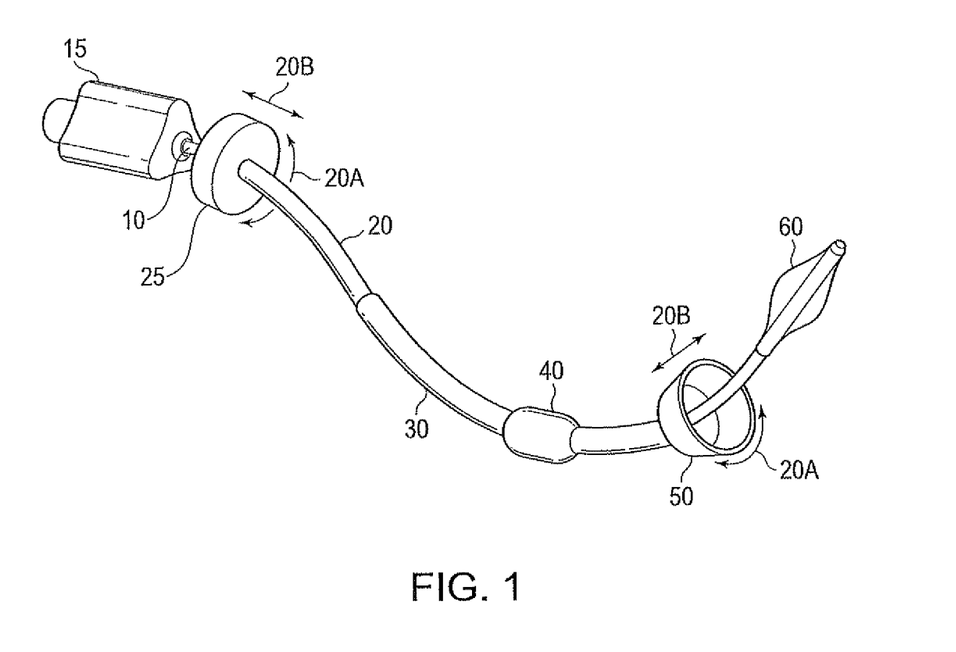
FIG. 1 illustrates a perspective view of a bipolar electrosurgical instrument that incorporates a colpotomy cup, uterine manipulator, and pneumoperitonial sealing device.

FIG. 1 illustrates a perspective view of a bipolar electrosurgical assembly. The bipolar electrosurgical assembly includes a first (or inner) shaft 10, a second (or intermediate) shaft 20 and a third (or outer) shaft 30. The first shaft 10 is a uterine manipulator, with a handle 15 near its proximal end, and an enlarged distal portion 60. The first shaft 10 typically is rigid or semi-rigid and is used by the surgeon to position the uterus once the distal portion 60 is inserted into the uterus. The second shaft 20 carries the colpotomy cup 50 near its distal end, and a controller 25 near its proximal end. In an exemplary embodiment of the bipolar electrosurgical assembly, the controller 25 is capable of controlling the insertion and retraction of the second shaft 20 in direction 20B (the longitudinal direction) and rotation 20A around an axis of the second shaft 20 of the colpotomy cup 50. The third shaft 30 carries a seal 40 for maintaining pneumoperitoneum.

Figure 2:
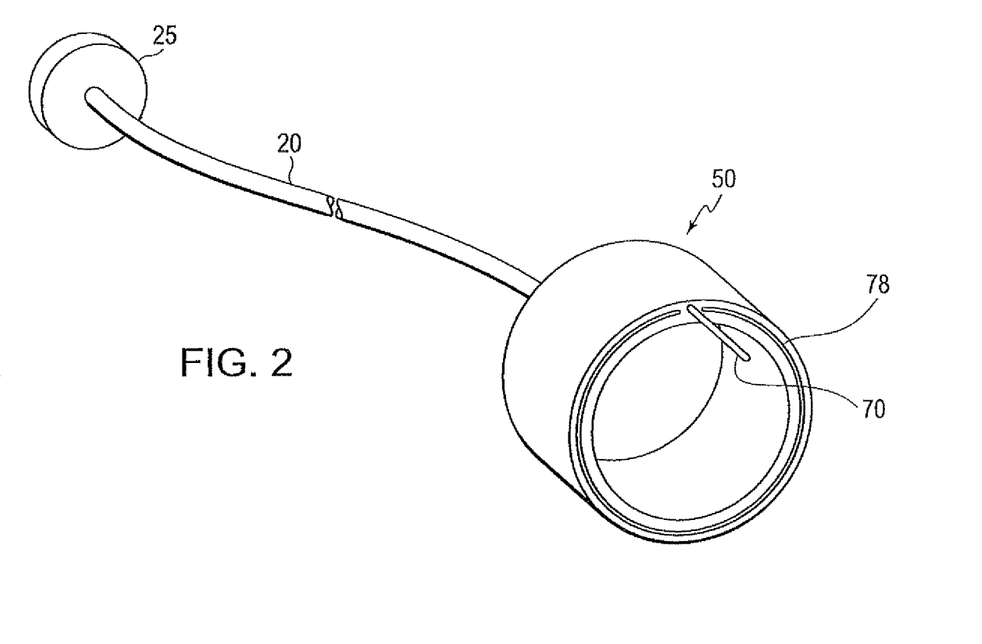
FIG. 2 illustrates a perspective view of the shaft bearing the colpotomy member in an embodiment.

FIG. 2 illustrates a perspective view of the second shaft of an exemplary embodiment of a bipolar electrosurgical assembly. The second shaft 20 has at its proximal end the controller 25 to manipulate the rotation and insertion and retraction of the second shaft including the colpotomy cup 50. In an embodiment according to FIG. 2, the first (active) electrode 70 is of a needle-type, and is placed on the distal rim of the colpotomy cup 50. The needle is electrically conductive, but preferably has an insulative layer over its distal-most end. Thus the cutting energy will be applied from a base portion of the needle electrode 70 located proximal of the distal tip of the needle. Alternatively, the entire needle could be an exposed, electrically conductive member. The cutting signal is supplied to the electrode 70 through an electrically conductive conductor, such as a wire, that is incorporated into the second shaft 20. The proximal end of the second shaft 20 includes an electrical connection by which the conductor for the electrode 70 is attachable to an energy source. In this embodiment, the second (return) electrode may be annular, disposed around a circumference of the distal rim radially inward from the first electrode 70, composed of just an arc near the first electrode 70, or cover all or most of the circumference of the rim. In the FIG. 2 embodiment, the second electrode 78 extends almost entirely around the rim of cup 50, and has the first electrode 70 positioned between opposing ends of the second electrode 78. The second electrode 78 is attached to another electrically conductive conductor, such as a wire, that is incorporated into and extends through the second shaft 20. The proximal end of the second shaft 20 also includes an electrical connector by which the conductor for the second electrode 78 is attachable to the return line of the energy source.

Figure 3:
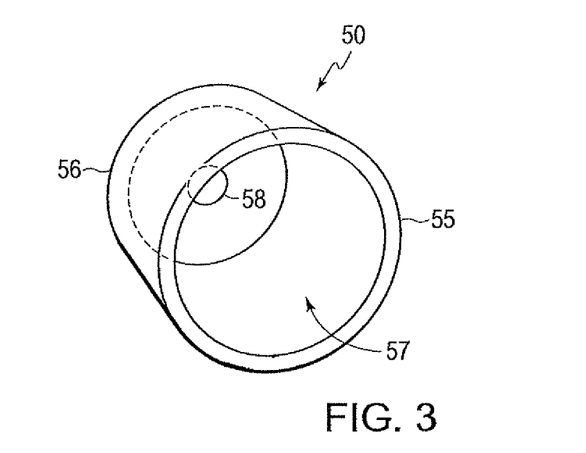
FIG. 3 illustrates a perspective view of the colpotomy cup in an embodiment.

FIG. 3 illustrates a perspective view of an embodiment of the colpotomy cup 50 that is provided on the second shaft 20. This embodiment of the colpotomy cup 50 has a narrower, proximal end 56 with an aperture 58 through which a shaft may pass. In some embodiments, the colpotomy cup 50 will have a hollow internal portion 57 in order to accommodate portions of a shaft, for example. In addition, a rim 55 is located at the distal, open end of the colpotomy cup 50 around the hollow internal portion 57.

Figure 4A:
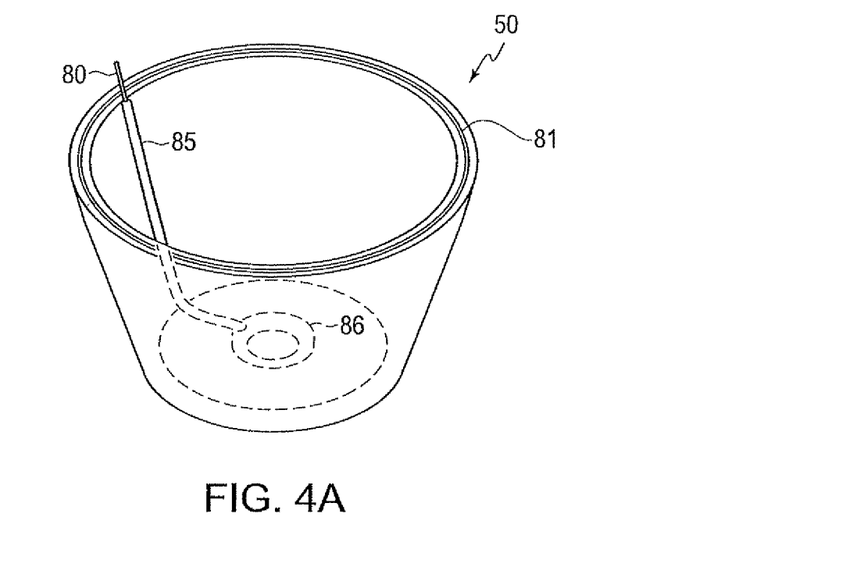
FIGS. 4A and 4B illustrate a perspective view and a plan view of a colpotomy member including the cup and an active electrode that moves relative to the cup.
Figure 4B:
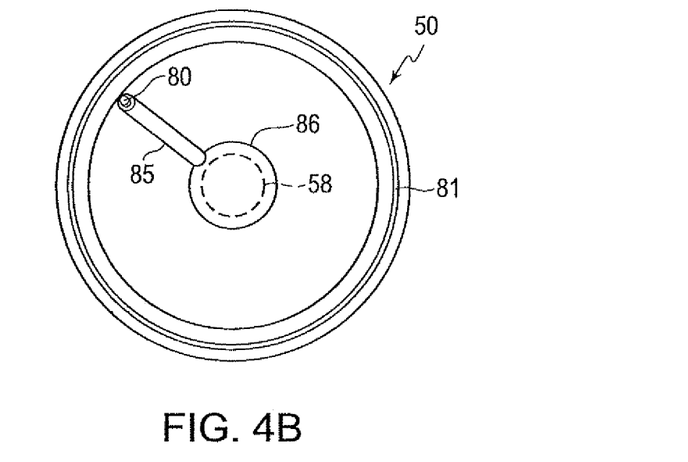

FIG. 4A illustrates a perspective view and FIG. 4B illustrates a plan view of an embodiment of the colpotomy cup 50 that can be provided on the second shaft 20. This embodiment disposes the first (active) electrode 80 at a distal end of an elongated portion 85 of a spindle 86 protruding from an aperture 58 in the proximal end of the colpotomy cup 50. This embodiment includes a second electrode 81 which is disposed on the rim 55 of the colpotomy cup 50. When using this embodiment, the surgeon rotates the spindle 86 while cutting energy is supplied to the first electrode 80 so that the first electrode 80 performs and completes an incision by rotating 360° about the axis of the second shaft. As an alternative to the embodiment shown in FIGS. 4A and 4B, in which the second (return) electrode 81 is fixed to the cup 50 while the first (active) electrode 80 rotates around the cup 50 with spindle 86, it is possible to provide both the active and return electrodes on a spindle (like spindle 86) that rotates relative to the cup about an axis of the cup. Embodiments that do not require rotation of the cup 50 are advantageous because, due to the cup's engagement with and support of the uterus, it can be difficult to rotate the cup 50.

Figure 5A:
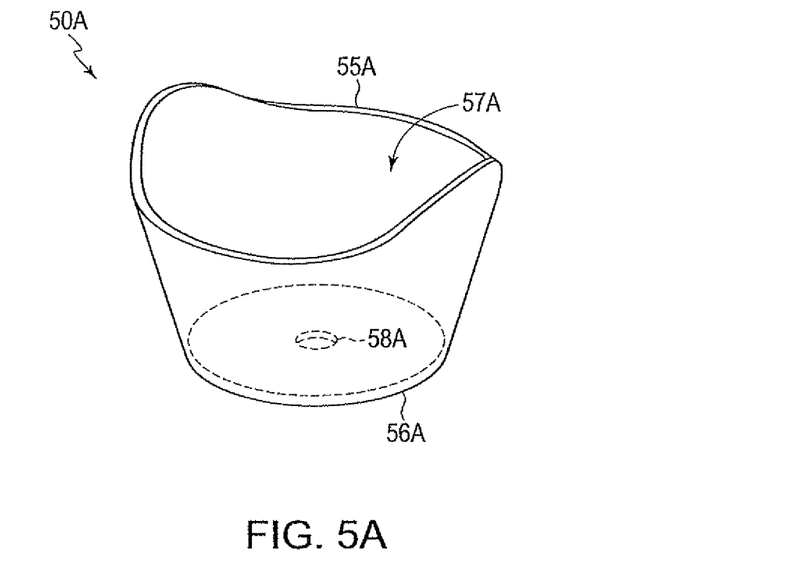
FIGS. 5A and 5B illustrate a perspective view and a top view of a portion of a rim of a colpotomy cup with an undulating (wavy) rim.
Figure 5B:
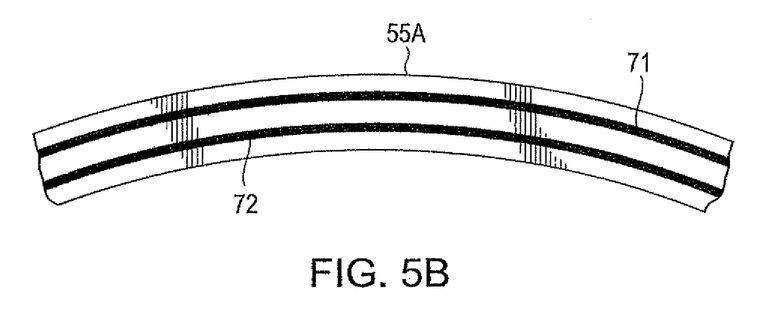

FIG. 5A illustrates a perspective view and FIG. 5B illustrates a plan view of a portion of a rim 55A of a colpotomy cup 50A. In this embodiment of the invention, the cup rim undulates and includes both the active and return electrodes. The colpotomy cup 50A has a narrower, proximal end 56A with an aperture 58A through which the second shaft 20 may pass. Similar to other embodiments, the colpotomy cup 50A has a hollow internal portion 57A and a distal rim 55A around the hollow internal portion 57A. However, according to an aspect of this embodiment, the rim 55A of the colpotomy cup 50A has an undulating surface, which varies in height along the rim 55A. A first electrode 71 and a second electrode 72 are arranged on the rim 55A of this embodiment. For example, the first electrode 71 can be on the radially outer edge of the rim 55A and the second electrode 72 can be on the radially inner edge of the rim 55A. A technique for using this embodiment includes advancing the colpotomy cup 50A longitudinally while applying a voltage differential between the first electrode 71 and the second electrode 72. When tissue makes contact with the first electrode 71, cutting energy is focused at the parts of the colpotomy cup 50A which are in contact with the tissue at that moment. As the colpotomy cup 50A is advanced longitudinally, first the highest part(s) of the rim 55A contact and cut tissue. As the colpotomy cup 55A is advanced further, the lower part(s) of the rim 55A contact and cut tissue.

Figure 6:
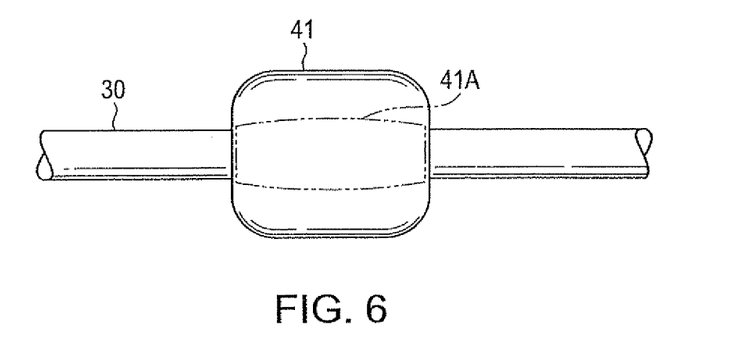
FIG. 6 illustrates a third shaft having a vaginal balloon that functions as a pneumoperitonial sealing device.
Figure 7:
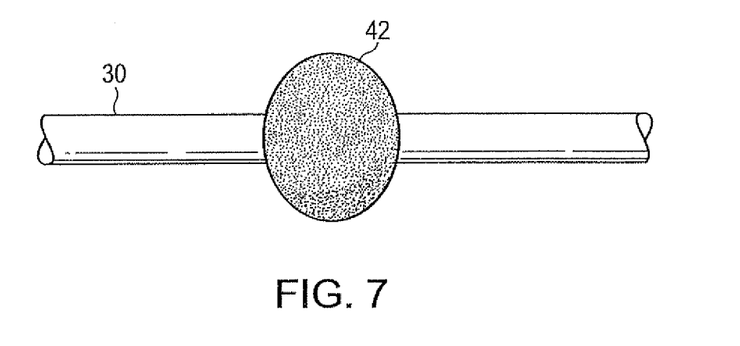
FIG. 7 illustrates a third shaft having a foam plug that functions as a pneumoperitonial sealing device.
Figure 8:
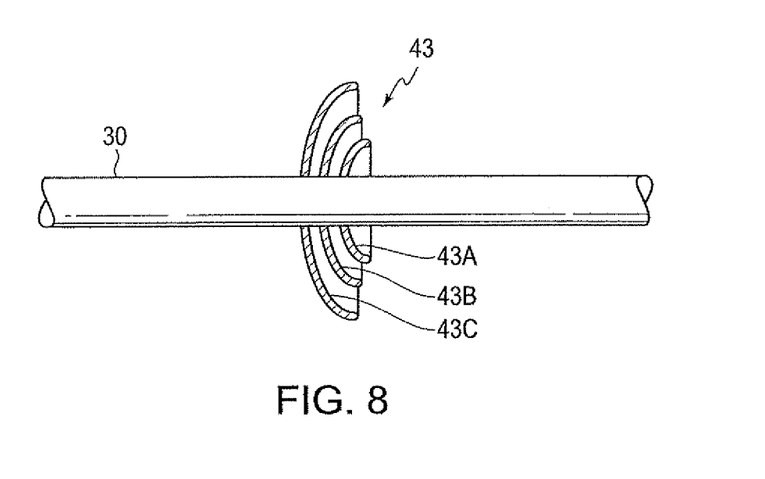
FIG. 8 illustrates a third shaft having a set of malleable discs that function as a pneumoperitonial sealing device.

FIGS. 6-8 illustrate different seals for maintaining pneumoperitoneum that may be located on the third shaft 30 in different embodiments of the invention. FIG. 6 illustrates an embodiment of the invention where the third shaft 30 includes a vaginal balloon 41 as the seal. An aspect of this embodiment of the seal is that the vaginal balloon can be in either a deflated state 41A or a fully inflated state 41, depending on the configuration that the physician desires. In another aspect of this embodiment, the third shaft 30 is slidably mounted over the second shaft and is capable of being positioned prior to inflation of the vaginal balloon 41. The third shaft includes a gas passage via which the balloon 41 can be inflated and deflated.

FIG. 7 illustrates an embodiment of the invention where the third shaft 30 includes a foam plug 42 as the seal. In an aspect of this embodiment, the third shaft 30 is slidably mounted over the second shaft and is capable of being positioned during surgery. The foam plug can be made of, for example, closed cell foam to form a soft malleable plug that is gas impermeable or an open cell foam with an external skin again making it gas impermeable. An important characteristic of the foam plug is to readily deflect for insertion without tissue injury and easy placement while subsequently conforming to the internal surface contours of the vaginal canal, in a manner so as to create the desired gas sealing or prevent the gas from leaking.

FIG. 8 illustrates an embodiment of the invention where the third shaft 30 includes malleable discs 43. The figure is illustrative and exhibits a configuration including three discs, 43A, 43B, and 43C. In an aspect of this embodiment, the malleable discs are configured so that the smallest disc, 43A, is the most distal. The discs increase in size in the proximal direction, with the most proximal, 43C, being the largest. The number, position, and size of the discs may be varied as required for a particular patient or application. The discs 43 are made of, for example, a soft malleable polymeric material or composite of materials such as LDPE or silicone that is gas impermeable. The malleability is critical for ease of insertion into the vaginal canal as well as limiting any tissue damage upon insertion and during placement.

Figure 9:
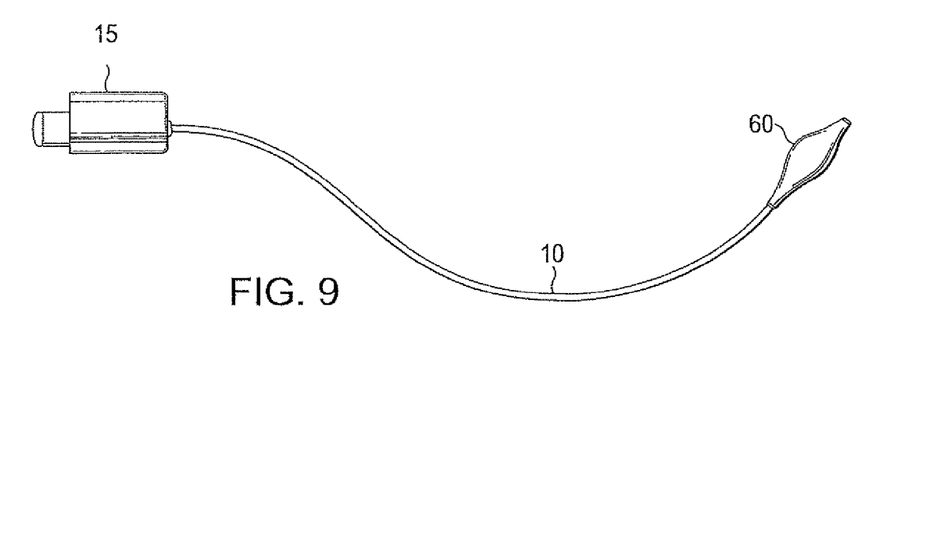
FIG. 9 illustrates a first shaft having a manipulator with an enlarged distal portion.

FIG. 9 illustrates an embodiment of the first shaft 10. In an aspect of this embodiment, a handle 15 for controlling the movement and orientation of the first shaft 10 is included near its proximal end. Also in this embodiment, an enlarged distal portion 60 is located near the distal end of the first shaft 10. The enlarged distal portion 60 of this embodiment may pass through the cervix, and enter the uterus for positioning of the uterus.

Figure 10:
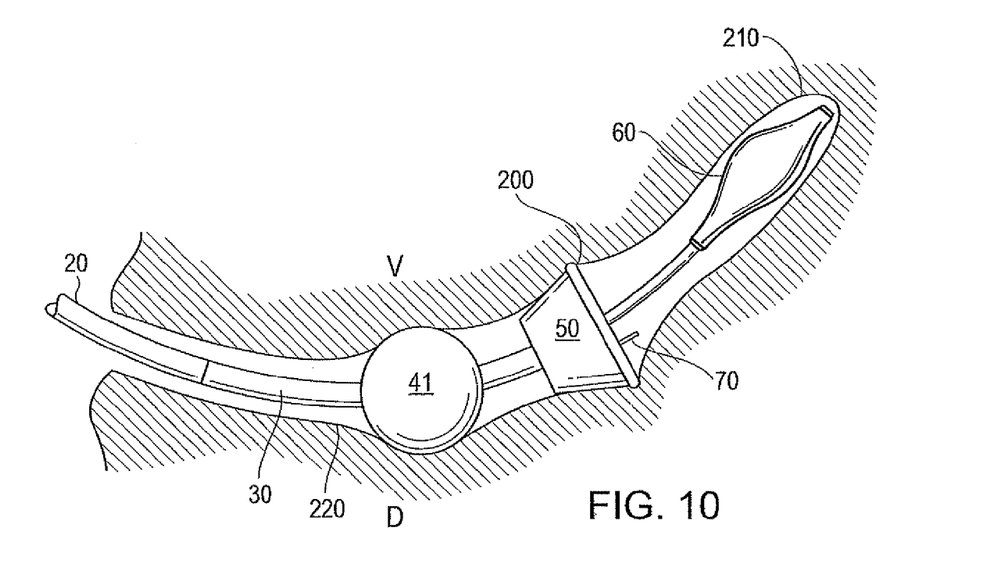
FIG. 10 illustrates a sagittal view of a patient's pelvic cavity, having the bipolar electrosurgical device placed in position to perform incision and resection.

FIG. 10 illustrates a sagittal view of a patient's pelvic cavity with an embodiment of the bipolar electrosurgical device in position to perform a TLH procedure. In this illustration, V represents the ventral side of the patient, and D represents the dorsal side of the patient. The enlarged distal portion 60 of the first shaft is located within the patient's uterus 210. The second shaft 20 has been inserted so that the colpotomy cup 50 is located at the cervico-vaginal junction 200. The third shaft 30 has a vaginal balloon 41 as a seal. The third shaft 30 has been inserted over and along the second shaft 20 such that the vaginal balloon 41 is located within the vaginal canal 220 and inflated so that it is making contact with the vaginal canal 220 and maintaining pneumoperitoneum during the laparoscopic procedure. The first electrode 70 is of a needle type, which is located on the rim of the colpotomy cup 50. In the illustrated embodiment, the second electrode (not visible) is located along the rim of the colpotomy cup 50, but not in direct contact with the first electrode 70.

Figure 11A:
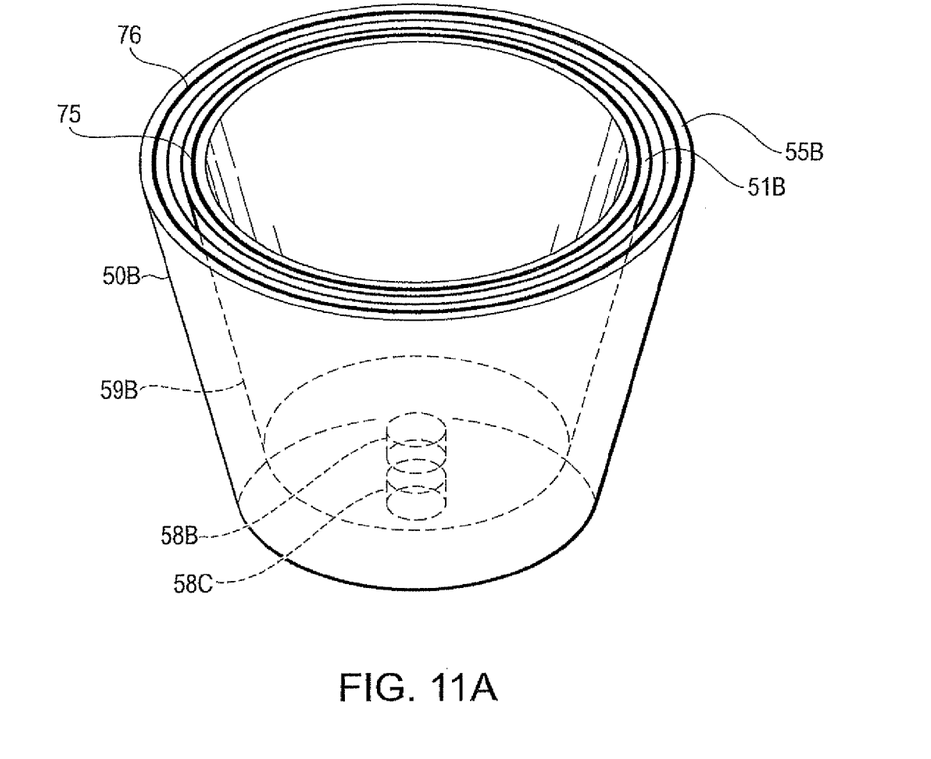
FIG. 11A illustrates a perspective, exploded view of a colpotomy cup with a rotating outer cup and a fixed inner cup.

In the embodiment illustrated in FIG. 10, the second shaft 20 is slidably and rotatably movable over the first shaft 10. The third shaft 30 is slidably and rotatably movable over the second shaft 20. In the embodiment illustrated in FIG. 11, rotation of the second shaft 20 controls rotation of the colpotomy cup 50. By this mechanism, an incision is formed along the cervico-vaginal junction 200 by the first electrode 70 as it rotates about the axis of the second shaft 20.

Figure 11B:
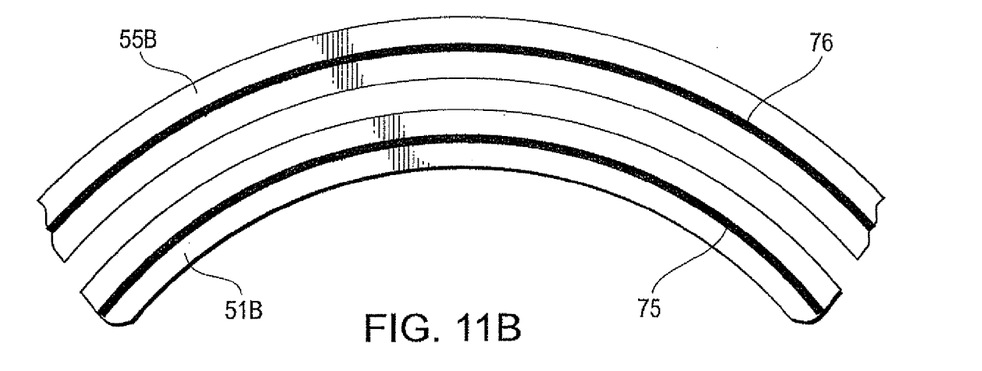
FIG. 11B illustrates a top, partial view of two rims of a rotating outer cup and a fixed inner cup.

FIGS. 11A and 11B illustrate an embodiment of a colpotomy cup with a fixed inner cup 59B and a rotatable outer cup 50B. Fixed inner cup 59B has an aperture 58B at its proximal end, and rotatable outer cup 50B has an aperture 58C at its proximal end. In this embodiment, the fixed inner cup 59B is fixedly attached to the second shaft 20. The rotatable outer cup 50B is rotatably attached to the second shaft 20. The first electrode 76 can be placed along the rim 55B of the rotatable outer cup 50B, and the second electrode 75 can be placed along the rim 51B of the fixed inner cup 59B. This embodiment performs the incision by rotating the rotatable outer cup 50B, while leaving the fixed inner cup 59B in a fixed position, while emitting energy from the first electrode 76 along the rim 55B of the rotatable outer cup 50B.

Figure 12:
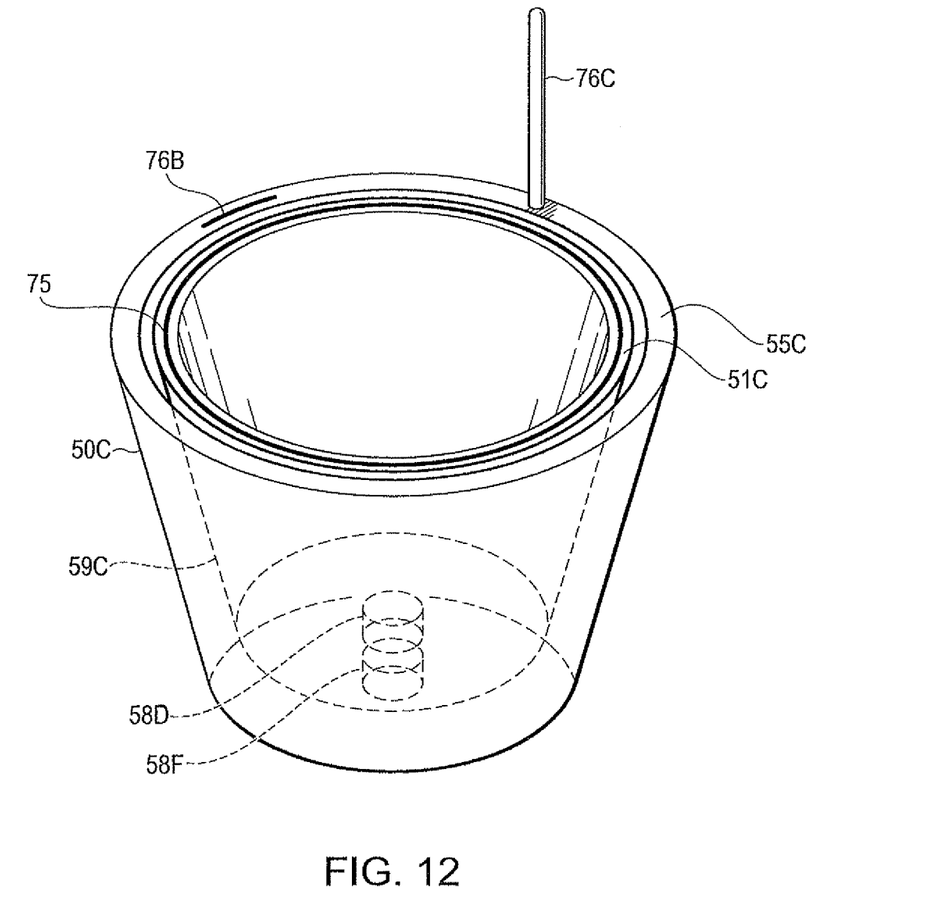
FIG. 12 illustrates a perspective, exploded view of a colpotomy cup with a rotating outer cup and a fixed inner cup.

FIG. 12 illustrates an embodiment of a colpotomy cup with a fixed inner cup 59C and a rotatable outer cup 50C. Fixed inner cup 59C has an aperture 58D at its proximal end, and rotatable outer cup 50C has an aperture 58F at its proximal end. In this embodiment, the fixed inner cup 59C is fixedly attached to the second shaft 20. The rotatable outer cup 50C is rotatably attached to the second shaft 20. The first electrode can take one of two forms. In the first form, the first electrode can be a portion 76B of the rim 55C of the rotatable outer cup 50C. Alternatively, the first electrode can be a needle electrode 76C placed on the rim 55C of the rotatable outer cup 50C. The second electrode 75 can be placed along the rim 51C of the fixed inner cup 59C. This embodiment performs the incision by rotating the rotatable outer cup 50C, while leaving the fixed inner up 59C in a fixed position, while emitting energy from the first electrode 76B or 76C placed along the rim 55C of the rotatable outer cup 50C.

The illustrated exemplary embodiments are intended to be illustrative and not limiting. Various changes may be made without departing from the spirit and scope of the invention. For example, a light can be included at the location of the electrodes to improve visibility during cutting. This would provide added safety to the user in ensuring that the electrode(s) is(are) positioned properly before cutting.

What is claimed is:

1. A bipolar electrosurgical assembly adapted for insertion into a vaginal cavity for use in female pelvic surgical procedures comprising:
   a first shaft, the first shaft having a proximal end, a distal end, and a manipulator adjacent to the distal end of the first shaft; and
   a second shaft disposed over the first shaft and having a proximal end, a distal end, a colpotomy cup mounted adjacent to the distal end of the second shaft, a first electrode and a second electrode, an open end of the colpotomy cup having a rim, wherein
   a voltage differential is applied between the first and second electrodes to vaporize tissue,
   the colpotomy cup has different heights at different points along the rim, and
   the first electrode and the second electrode are located along distal edges of the rim.

2. A bipolar electrosurgical assembly adapted for insertion into a vaginal cavity for use in female pelvic surgical procedures comprising:
   a first shaft, the first shaft having a proximal end, a distal end, and a manipulator adjacent to the distal end of the first shaft;
   a second shaft disposed over the first shaft and having a proximal end, a distal end, a colpotomy cup mounted adjacent to the distal end of the second shaft, a first electrode and a second electrode, an open end of the colpotomy cup having a rim; and
   a needle that protrudes from the rim of the colpotomy cup, wherein
   the needle is the first electrode,
   the second electrode is located along the rim of the colpotomy cup, and
   a voltage differential is applied between the first and second electrodes to vaporize tissue.

3. The bipolar electrosurgical assembly according to claim 2, wherein
   the second electrode extends almost entirely around the rim of the colpotomy cup and has first and second ends, and
   the needle is disposed on the rim between the first and second ends of the second electrode.

4. The bipolar electrosurgical assembly according to claim 2, further comprising:
   a third shaft disposed over the second shaft and having a proximal end, a distal end, and a seal attached adjacent to the distal end of the third shaft, wherein
   the seal is proximate of the colpotomy cup, and
   the seal makes a gas-tight seal in the vaginal cavity.

5. The bipolar electrosurgical assembly according to claim 2, wherein
   the second shaft including the colpotomy cup is capable of rotating around the first shaft.

6. The bipolar electrosurgical assembly according to claim 1, further comprising:
   a third shaft disposed over the second shaft and having a proximal end, a distal end, and a seal attached adjacent to the distal end of the third shaft, wherein
   the seal is proximate of the colpotomy cup, and
   the seal makes a gas-tight seal in the vaginal cavity.

7. The bipolar electrosurgical assembly according to claim 6, wherein the seal includes a vaginal balloon.

8. The bipolar electrosurgical assembly according to claim 6, wherein the seal includes a foam plug.

9. The bipolar electrosurgical assembly according to claim 6, wherein the seal includes malleable discs.

10. The bipolar electrosurgical assembly according to claim 1, wherein
    the second shaft including the colpotomy cup is capable of rotating around the first shaft.

11. The bipolar electrosurgical assembly according to claim 1, wherein
    the first and second electrodes each extend entirely around the rim at the open end of the colpotomy cup.

12. A bipolar electrosurgical assembly adapted for insertion into a vaginal cavity for use in female pelvic surgical procedures comprising:
    a first shaft, the first shaft having a proximal end, a distal end, and a manipulator adjacent to the distal end of the first shaft;
    a second shaft disposed over the first shaft and having a proximal end, a distal end, a colpotomy cup mounted adjacent to the distal end of the second shaft, a first electrode and a second electrode, an open end of the colpotomy cup having a rim; and
    an elongated member extending along the second shaft, the first electrode disposed on the elongated member, wherein
    a voltage differential is applied between the first and second electrodes to vaporize tissue.

13. The bipolar electrosurgical assembly of claim 12, wherein
    the elongated member is a spindle that is rotatable around an axis of the second shaft, independently of the colpotomy cup on which the second electrode is disposed.

14. The bipolar electrosurgical assembly according to claim 12, further comprising:
    a third shaft disposed over the second shaft and having a proximal end, a distal end, and a seal attached adjacent to the distal end of the third shaft, wherein
    the seal is proximate of the colpotomy cup, and
    the seal makes a gas-tight seal in the vaginal cavity.

15. The bipolar electrosurgical assembly according to claim 12, wherein
    the second shaft including the colpotomy cup is capable of rotating around the first shaft.

16. A bipolar electrosurgical assembly adapted for insertion into a vaginal cavity for use in female pelvic surgical procedures comprising:
    a first shaft, the first shaft having a proximal end, a distal end, and a manipulator adjacent to the distal end of the first shaft;
    a second shaft disposed over the first shaft and having a proximal end, a distal end, a colpotomy cup mounted adjacent to the distal end of the second shaft, a first electrode and a second electrode, an open end of the colpotomy cup having a rim; and
    a second cup fixedly mounted to the second shaft, radially inward from the colpotomy cup, wherein
    an open end of the second cup has a second rim,
    the first electrode is located along the rim of the colpotomy cup,
    the colpotomy cup is rotatable independently of the second cup, and
    a voltage differential is applied between the first and second electrodes to vaporize tissue.

17. The bipolar electrosurgical assembly according to claim 16, further comprising:
    a third shaft disposed over the second shaft and having a proximal end, a distal end, and a seal attached adjacent to the distal end of the third shaft, wherein
    the seal is proximate of the colpotomy cup, and
    the seal makes a gas-tight seal in the vaginal cavity.

18. The bipolar electrosurgical assembly according to claim 16, wherein
the second shaft including the colpotomy cup is capable of rotating around the first shaft.

* * * * *